(12) United States Patent
Dacey

(10) Patent No.: US 8,292,076 B2
(45) Date of Patent: Oct. 23, 2012

(54) SEALED POUCHES FOR MEDICAL DEVICES HAVING TEXTURED OPENING FLANGES AND METHODS THEREFOR

(75) Inventor: Denise Marie Dacey, Glen Gardner, NJ (US)

(73) Assignee: Ethicon, Inc., Somerville, NJ (US)

( * ) Notice: Subject to any disclaimer, the term of this patent is extended or adjusted under 35 U.S.C. 154(b) by 290 days.

(21) Appl. No.: 12/820,401

(22) Filed: Jun. 22, 2010

(65) Prior Publication Data

US 2011/0308981 A1    Dec. 22, 2011

(51) Int. Cl.
*A61B 17/06* (2006.01)
*B65D 33/00* (2006.01)

(52) U.S. Cl. .......... 206/438; 206/370; 220/270; 383/35; 383/210

(58) Field of Classification Search .......... 206/63.5, 206/438, 363, 364, 368, 369, 370; 220/260, 220/265, 266, 270; 383/120, 210, 35
See application file for complete search history.

(56) References Cited

U.S. PATENT DOCUMENTS

| | | | |
|---|---|---|---|
| 3,036,756 A | 5/1962 | Lieschke | |
| 3,613,879 A * | 10/1971 | Kemble | 206/438 |
| 3,724,651 A | 4/1973 | Link | |
| 3,926,311 A | 12/1975 | Laske | |
| 3,995,739 A * | 12/1976 | Tasch et al. | 383/210 |
| 4,206,844 A | 6/1980 | Thukamoto et al. | |
| 5,082,112 A * | 1/1992 | Dunklee | 206/363 |
| 5,253,754 A | 10/1993 | Soodak | |
| 5,353,929 A * | 10/1994 | Foster | 206/364 |
| 5,386,908 A * | 2/1995 | Sinn | 206/363 |
| 5,699,909 A * | 12/1997 | Foster | 206/370 |
| 5,878,549 A | 3/1999 | Littman et al. | |
| 6,234,676 B1 | 5/2001 | Galomb et al. | |
| 6,874,938 B2 | 4/2005 | Price et al. | |
| 8,061,897 B2 * | 11/2011 | Ichikawa et al. | 383/210 |
| 2005/0189252 A1 * | 9/2005 | Naylor et al. | 206/363 |
| 2008/0063325 A1 | 3/2008 | Miller et al. | |
| 2009/0200198 A1 | 8/2009 | Guelzow et al. | |
| 2010/0078347 A1 * | 4/2010 | Brinker | 206/438 |

* cited by examiner

*Primary Examiner* — Luan K Bui
(74) *Attorney, Agent, or Firm* — Doherty & Charney LLC

(57) ABSTRACT

A sealed foil pouch has a textured opening flange and includes first and second foil sheets having opposing inner surfaces joined together by a seal for defining a sealed area of the pouch located inside the seal and an unsealed area of the pouch located outside the seal. The sealed pouch includes a textured opening flange located adjacent an edge of the pouch for peeling the first and second foil sheets away from one another for breaking the seal and opening the sealed pouch. The textured opening flange is located within the unsealed area of the pouch and includes at least one roughened surface formed on at least one of the first and second sheets. A leg of the seal passes through the textured opening flange. The roughened surface makes it easier to break the leg of the seal for pulling the sheets apart.

20 Claims, 12 Drawing Sheets

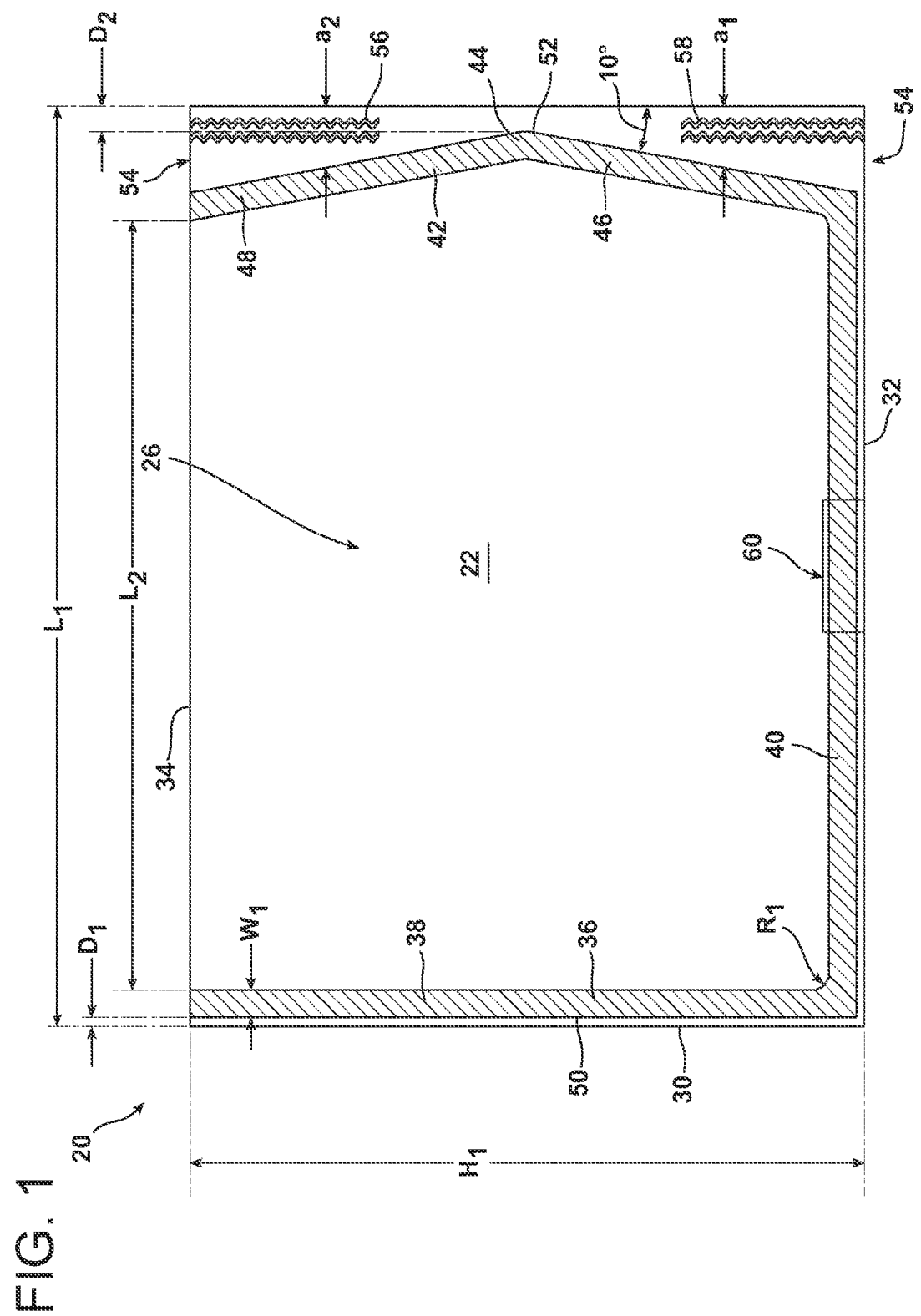

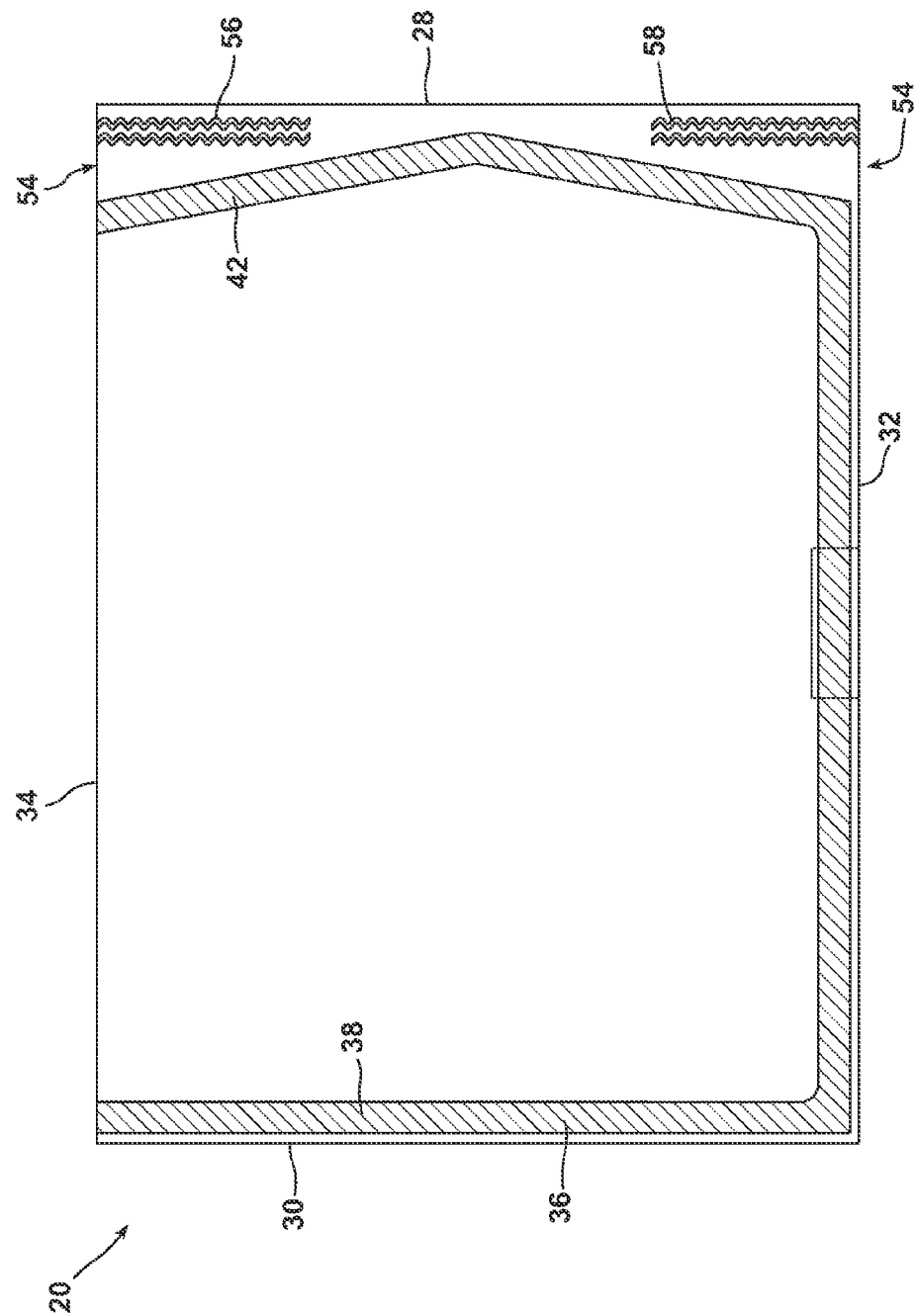

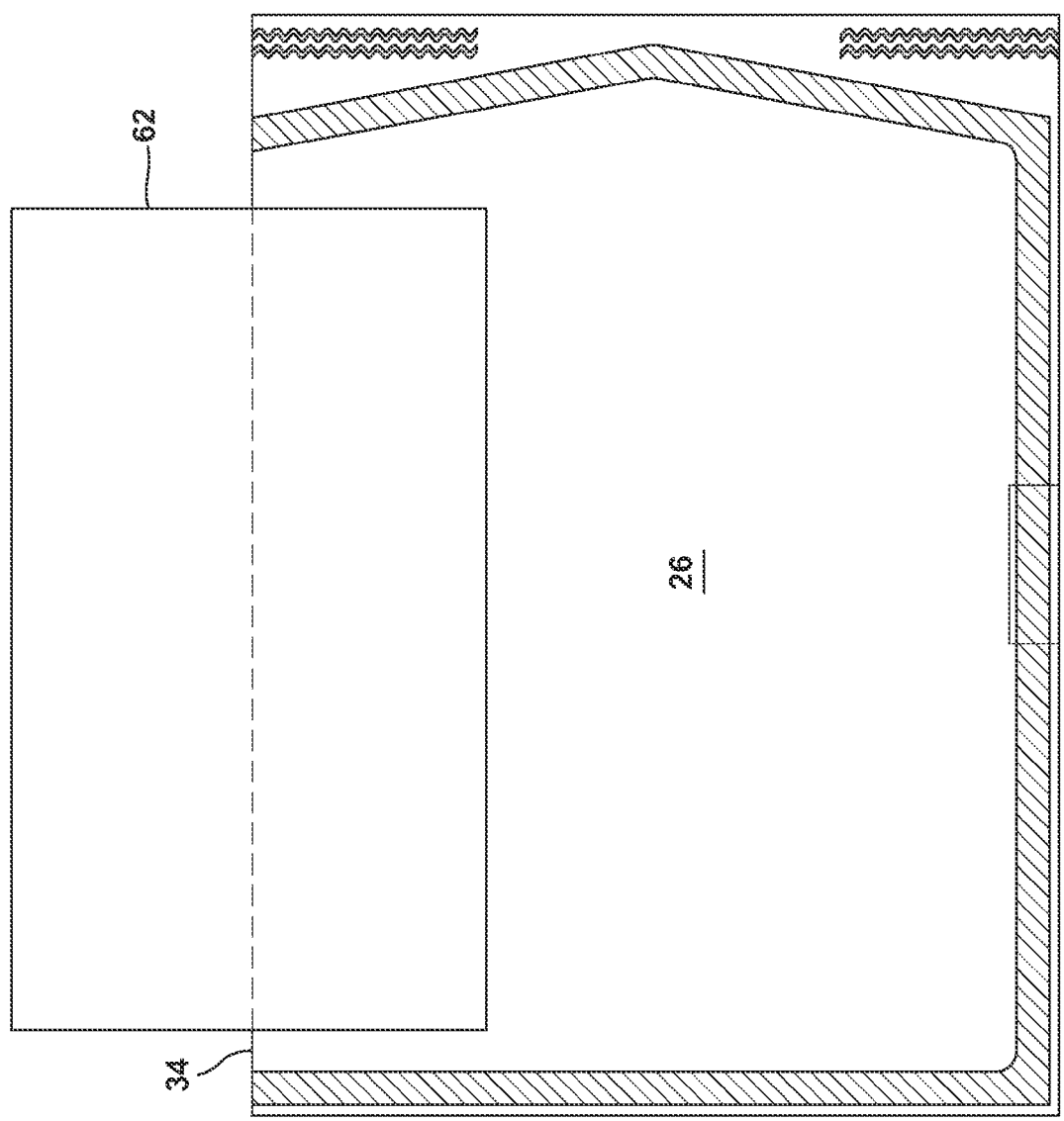

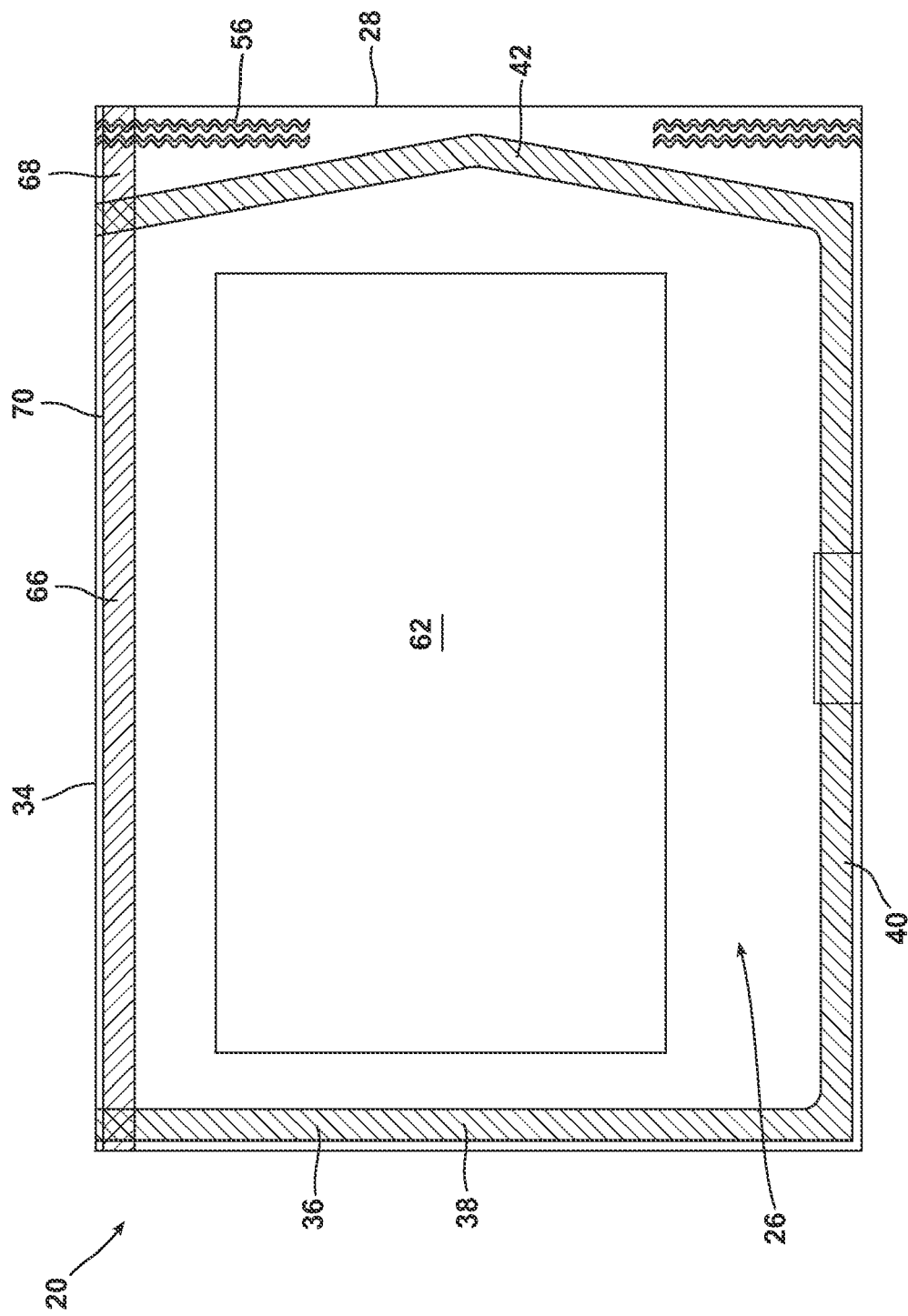

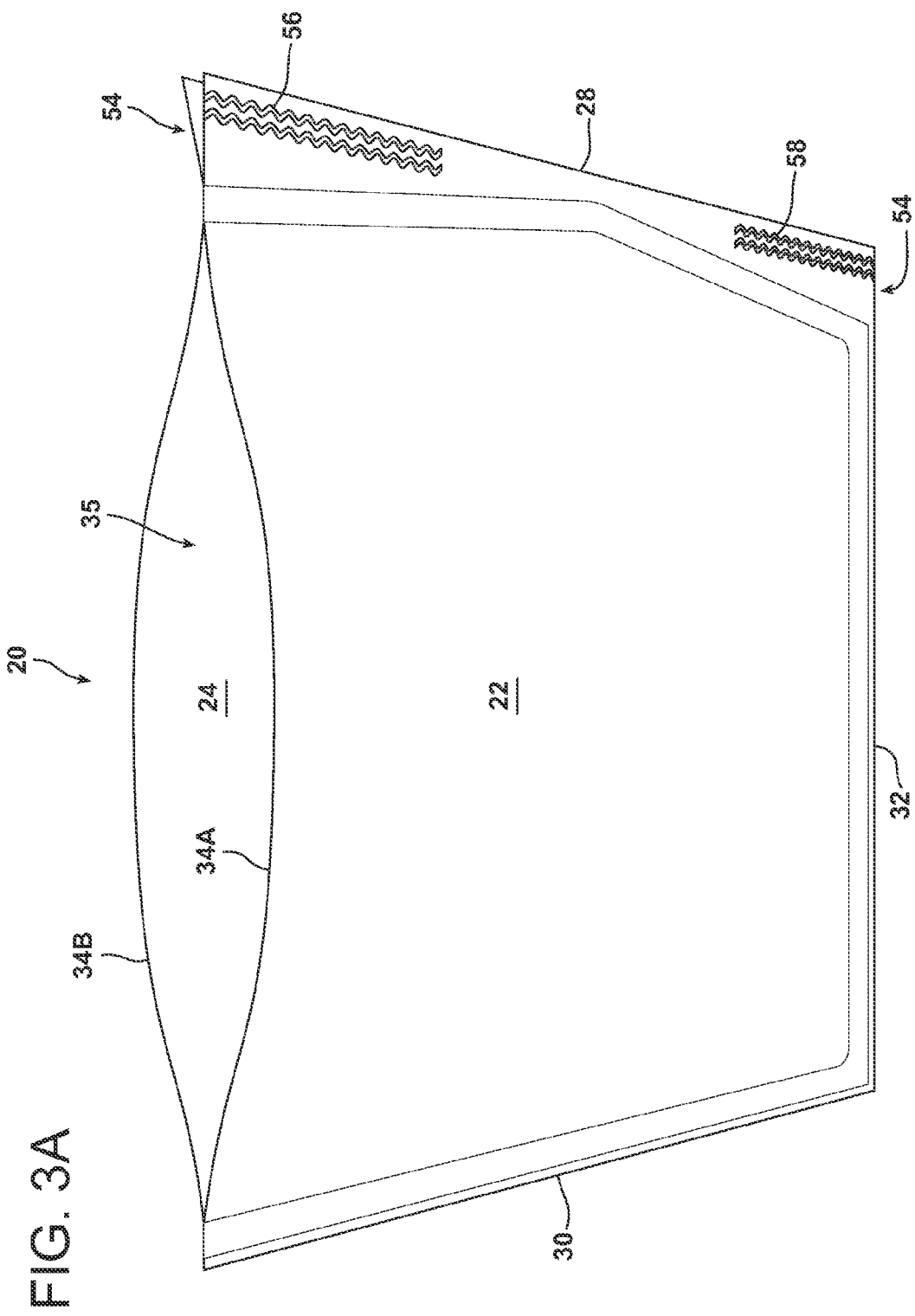

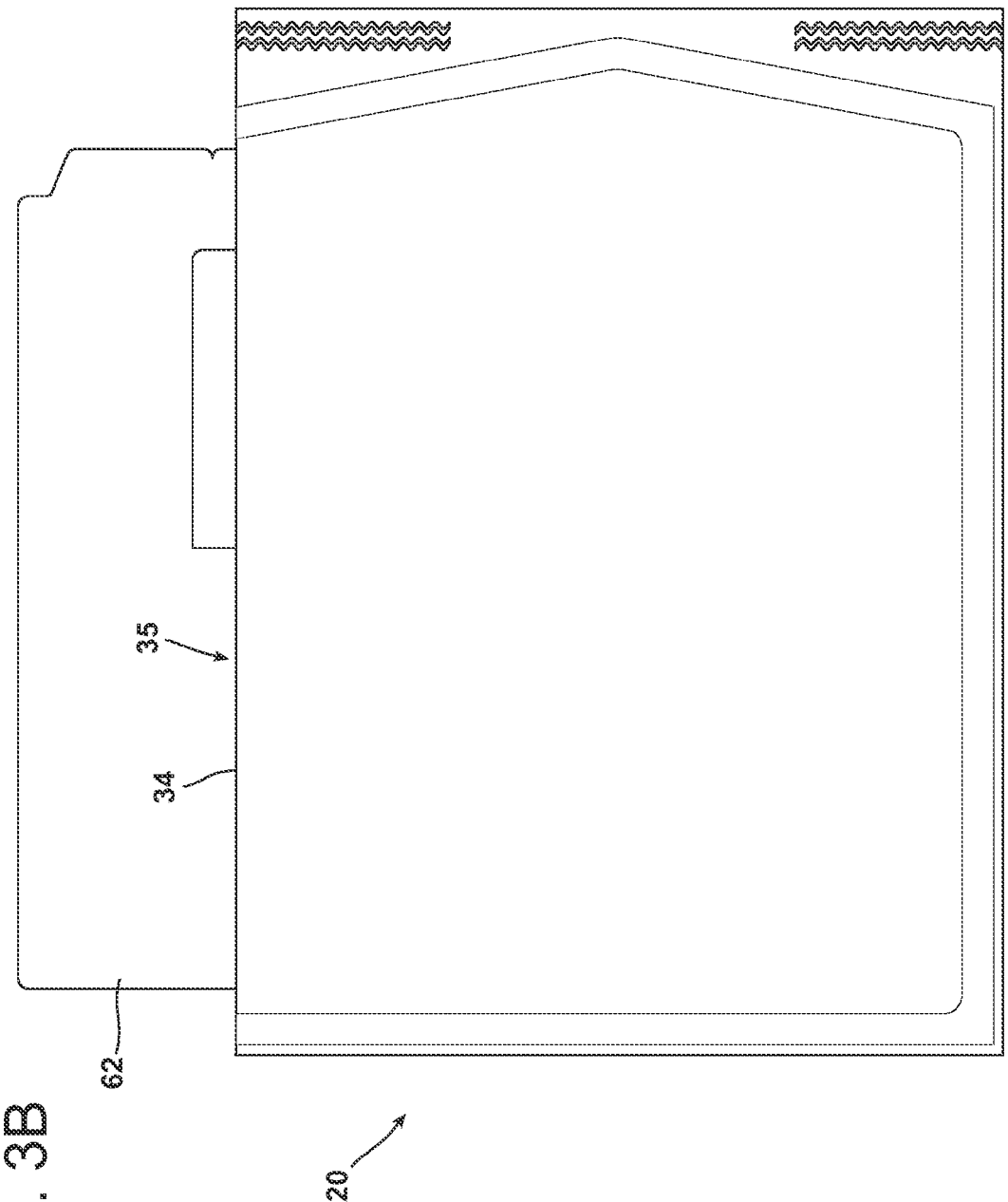

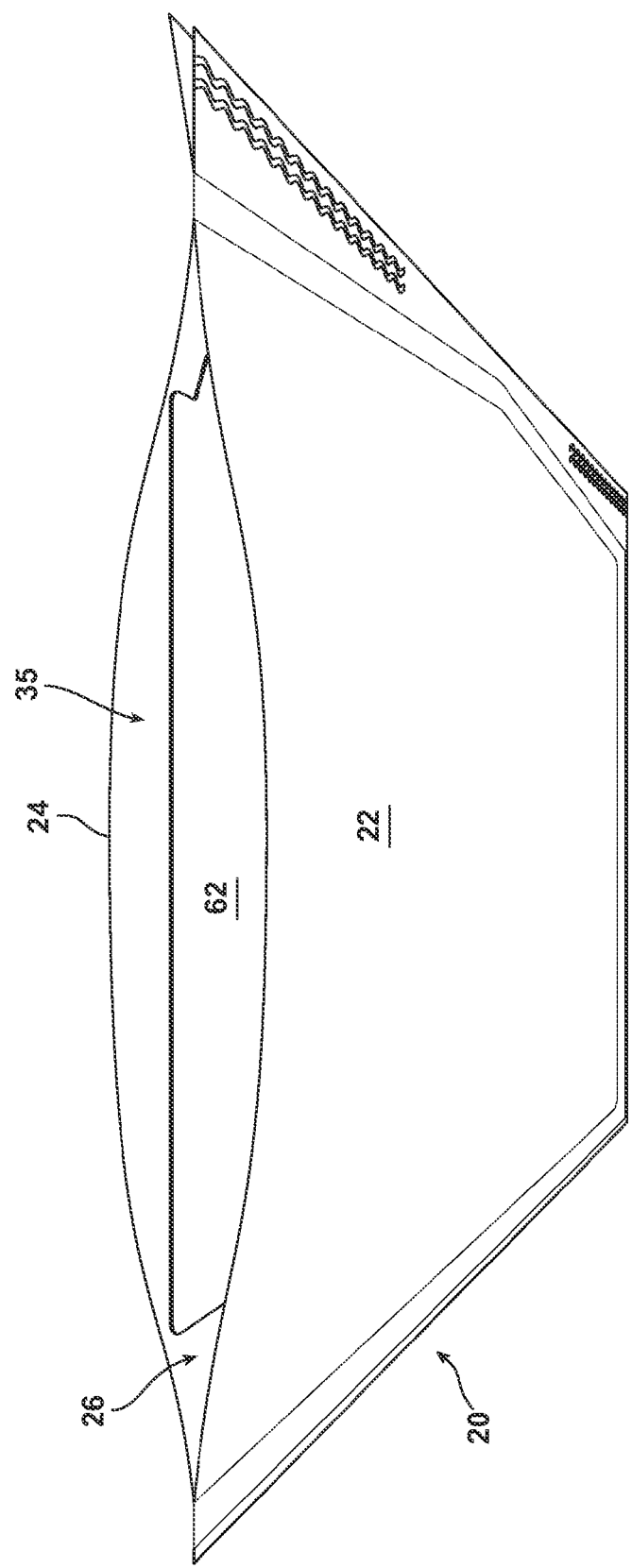

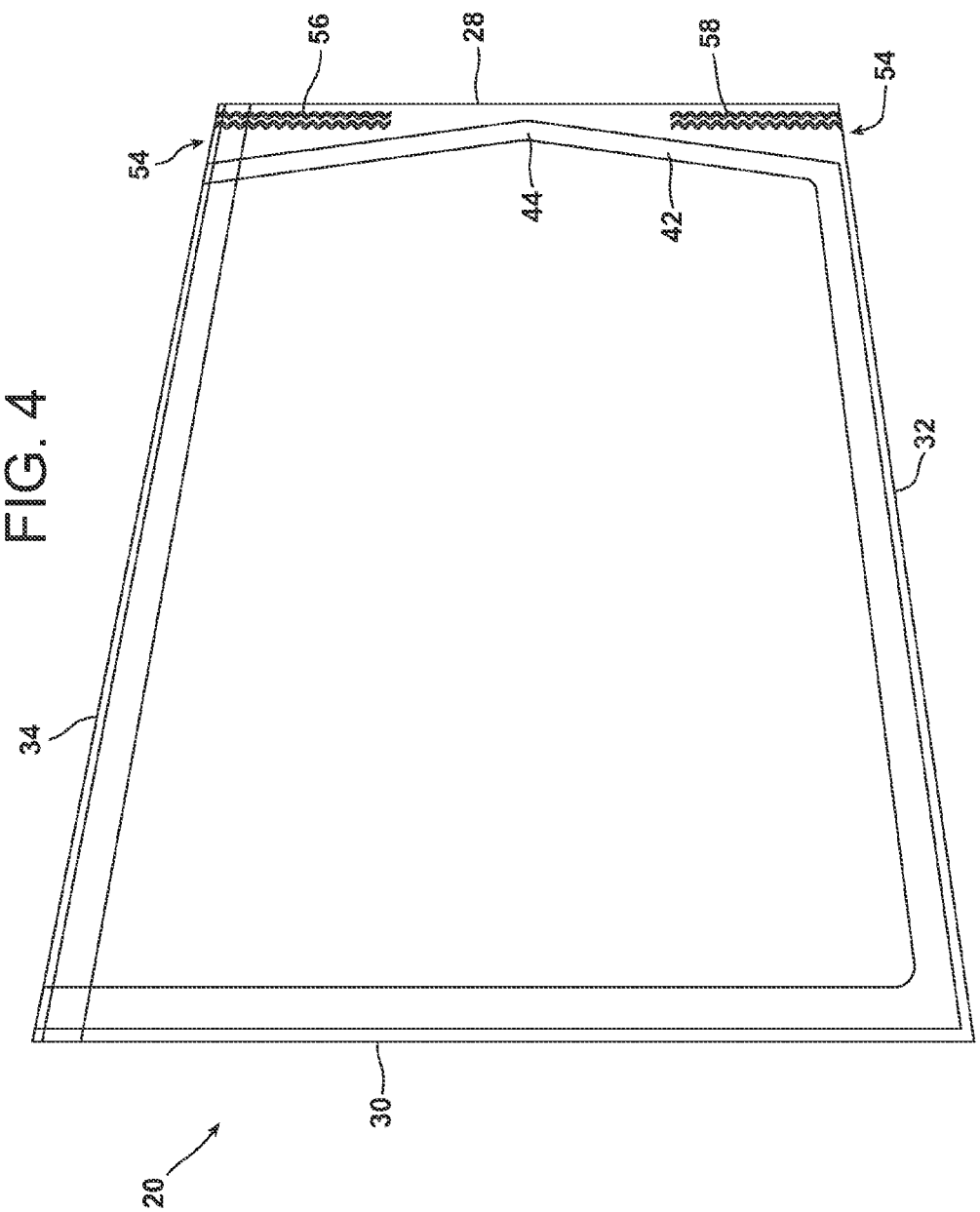

SEALED POUCHES FOR MEDICAL DEVICES HAVING TEXTURED OPENING FLANGES AND METHODS THEREFOR

BACKGROUND OF THE INVENTION

1. Field of the Invention

The present invention is generally related to medical devices, and is more specifically related to packages for medical devices.

2. Description of the Related Art

During surgical procedures, great care is taken to prevent contamination of the surgical tools and medical devices used during the course of an operation. An operating team typically includes at least one member whose function is to open packages containing surgical tools and medical devices and to present them to a sterile nurse or surgeon in a manner whereby they remain in a sterile condition.

There have been many efforts directed to providing packages for medical devices that allow for efficient opening of the package and presentation of the medical devices to surgical personnel in a sterile condition. One type of package provides a color-marked envelope that indicates the area to be torn off to provide an access opening to the contents within the envelope without affecting the sterility of the contents. Another type of package provides a tear string that may be pulled to open the envelope so that the contents may be removed using forceps or another similar tool.

Packages for medical devices have also been provided having integral tear strips, which, when removed, not only sever the packages but provide delaminated margins on the exterior surfaces of the packages adjacent to the severed edges. It has been found that great care must be taken in the removal of the tear strip to avoid failure of the strip before the de-lamination is completed and the package is completely open. While a sterile surface area adjacent to the access area is provided by this method, the sterile area is limited in width to the delaminated margin which, of necessity, must be narrowed to prevent failure of the tear strip. Accordingly, the degree of care required in removing the contents of the package without contacting an unsterile surface surrounding the access area is, while lessened, still significant.

Commonly assigned U.S. Pat. No. 3,724,651 to Link discloses a peelable package for containing surgical tools and medical that may be sealed and sterilized within the package and subsequently removed therefrom with a minimum probability of contamination by the unsterile outer surfaces of the package. The package has two panels sealed together at their marginal portions to form a chamber therebetween having a sealed mouth and adjacent sealed edges. A section of the sealed marginal portions of one panel, extending across the mouth and along the adjacent edges of the package, is weakened, by scoring, so that upon opening the package, the weakened section of the panel will delaminate to the depth of the scoring in preference to yielding at the seal. The package is also provided with tabs extending beyond a sealed mouth. The tabs include bending scores which allow them to be folded away from the sterile portions of the package and additionally initiate the delamination of the panel when opening the package.

U.S. Pat. No. 5,878,549 to Littman et al. discloses an easy open tear control package, such as a pouch, made from a film of polymeric barrier material. The easy open tear control feature is formed from roughening portions of the outer and inner surface of the films, prior to fabricating the films into a package. The roughened portion is on one face or on each face of the package and is at least a full width of the seal when the film is made into the package. The roughened portion can extend the entire width of the package and can be of any desired length. With the package disclosed in the '549 patent, it is difficult to rapidly remove the contents of the package while maintaining sterility.

In spite of the above advances, there remains a need for an improved package for medical devices that is easy to open and that ensures maintenance of a strong seal prior to opening for maintaining the contents inside the package in a sterile environment. There also remains a need for a package that provides a clear indication of the end of the package that is to be opened. In addition, there remains a need for an improved package, such as a foil pouch, having an embossed or roughened surface having a particular pattern that reduces the chances for counterfeiting. Moreover, there remains a need for a package that facilitates loading a medical device inside the package.

SUMMARY OF THE INVENTION

In one embodiment, a pouch having a textured opening flange preferably includes first and second sheets, such as first and second foil sheets, having opposing inner surfaces joined together by a seal for defining a sealed area of the pouch located inside the seal and an unsealed area of the pouch located outside the seal. The pouch desirably includes a textured opening flange located adjacent an edge of the pouch for peeling the first and second sheets away from one another for breaking the seal and opening the sealed pouch. The textured opening flange is preferably located within the unsealed area of the pouch and includes at least one roughened surface formed on at least one of the first and second sheets.

In one embodiment, at least a portion of the seal extends through a roughened surface of the textured opening flange. In one embodiment, the portion of the seal passing through a roughened surface preferably lies outside the sealed area of the pouch so that the integrity of the sealed area is not weakened or breached. Although the present invention is not limited by any particular theory of operation, seal strength data shows that the roughened surface reduces the amount of force required the peel apart the first and second sheets where the seal holds the first and second sheets together.

When prior art pouches for medical devices are cut, the cutting process may bring the two sheets of the pouch close together, making it difficult to separate the sheets from one another when opening the pouch, especially when wearing gloves. In the present invention, an opening flange area of at least one of the sheets is embossed or roughened to form a roughened surface that physically separates the two sheets of the pouch from one another. The physical separation of the sheets at the opening flange area makes it easier for medical personnel to separate the sheets from one another, which, in turn, makes it easier to grasp the two sheets for peeling the sheets apart.

In one embodiment, the pouch preferably includes a leading edge, a trailing edge, a lower edge and an upper edge, whereby the textured opening flange is located adjacent the leading edge of the pouch. In one embodiment, the textured opening flange is located between the seal and the leading edge of the pouch. In one embodiment, the at least one roughened surface is adjacent the leading edge of the pouch. The at least one roughened surface preferably extends parallel with the leading edge of the pouch. In one embodiment, the at least one roughened surface desirably includes a first roughened section extending from the upper edge of the pouch and a second roughened section extending from the lower edge of the pouch.

In one embodiment, the at least one roughened surface preferably includes a first roughened surface formed in the first sheet and a second roughened surface formed in the second sheet that is aligned with the first roughened surface. The at least one roughened surface desirably includes deformations formed in at least one surface of at least one of the first and second sheets.

The at least one roughened surface is desirably located outside the seal so that the integrity and strength of the seal remains unaffected by the presence of the roughened surface. The at least one roughened surface preferably enables opposing edges of the first and second sheets to be peeled away from one another for commencing an opening of the package.

The seal may be formed using well-known techniques including adhesive, heat, or pressure and combinations thereof. In one embodiment, the seal preferably includes a first leg extending adjacent the trailing edge of the pouch, a second leg extending adjacent the lower edge of the pouch, a third leg extending adjacent the leading edge of the pouch, and a fourth leg extending adjacent the upper edge of the pouch. In one embodiment, the first, second and third legs of the seal have outer perimeters that are spaced from the respective trailing, lower and upper edges of the pouch. In one embodiment, the outer perimeter of the first leg of the seal is spaced about 2-5 mm from the trailing edge of the pouch, the outer perimeter of the second leg of the seal is spaced about 2-5 mm from the lower edge of the pouch, and the outer perimeter of the fourth leg of the seal is spaced about 2-5 mm from the upper edge of the pouch.

In one embodiment, the leading edge of the pouch preferably includes a first end located adjacent the upper edge of the pouch, a second end located adjacent the lower edge of the pouch and a center located between the first and second ends of the leading edge. In one embodiment, the third leg of the seal is preferably non-linear and includes an apex aligned with the center of the leading edge. The non-linear third leg desirably includes a first section extending between the apex of the third leg and the upper edge of the pouch and a second section extending between the apex of the third leg and the lower edge of the pouch. In one embodiment, the first section of the third leg preferably extends along an axis that defines a first angle with the leading edge of the pouch and the second section of the third leg extends along a second axis that defines a second angle with the leading edge of the pouch. The first and second angles may be about 10-20° and more specifically about 15°.

In one embodiment, a sealed foil pouch having a textured opening flange preferably includes first and second foil sheets having opposing inner surfaces joined together by a seal for defining a sealed area of the foil pouch located inside the seal and an unsealed area of the foil pouch located outside the seal. The sealed foil pouch preferably has a textured opening flange located adjacent an edge of the foil pouch for peeling the first and second foil sheets away from one another for breaking the seal and opening the sealed foil pouch for removing the contents therein. In one embodiment, the textured opening flange is desirably located within the unsealed area of the foil pouch and includes at least one roughened surface formed on at least one of the first and second foil sheets.

In one embodiment, a medical device is preferably disposed within the sealed area of the foil pouch. The sealed area is preferably sterile for maintaining the medical device in a sterile state. The medical device is desirably removable from the foil pouch by peeling the first and second foil sheets away from one another for breaking the seal and opening the sealed foil pouch.

In one embodiment, the textured opening flange preferably includes a first pull tab located on the first foil sheet and a second pull tab located on the second foil sheet. In one embodiment, the first and second pull tabs are desirably peelable away from one another for facilitating grasping of the first and second foil sheets, thereby providing enhanced leverage on the sheets for peeling the sheets away from one another.

In one embodiment, the seal that joins the first and second foil sheets desirably includes a first leg extending adjacent the trailing edge of the foil pouch, a second leg extending adjacent the lower edge of the foil pouch, a third leg extending adjacent the leading edge of the foil pouch and a fourth leg extending adjacent the upper edge of the foil pouch. In one embodiment, the first, second and third legs of the seal preferably have outer perimeters that are spaced from the respective trailing, lower and upper edges of the foil pouch. In one embodiment, the leading edge of the foil pouch preferably includes a first end located adjacent the upper edge of the foil pouch, a second end located adjacent the lower edge of the foil pouch and a center located between the first and second ends of the leading edge. In one embodiment, the third leg of the seal is preferably non-linear and includes an apex aligned with the center of the leading edge, a first section extending between the apex of the third leg and the upper edge of the foil pouch and a second section extending between the apex of the third leg and the lower edge of the foil pouch. In one embodiment, the first section of the third leg preferably extends along an axis that defines a first angle with the leading edge of the foil pouch and the second section of the third leg preferably extends along a second axis that defines a second angle with the leading edge of the foil pouch.

In one embodiment, a method of making a sealed foil pouch having a textured opening flange preferably includes providing first and second foil sheets having inner surfaces, and forming a partial seal between the inner surfaces of the first and second foil sheets to define a sealed area located inside the seal, an unsealed area located outside the seal, and a pouch opening extending between the unsealed area and the sealed area. The method desirably includes roughening a surface of at least one of the first and second foil sheets, whereby the roughened surface is located within the unsealed area of the foil pouch. In one embodiment, the method preferably includes filling the pouch opening with a medical tool or medical device, such as a tissue supporting implant, and forming a supplemental seal between the inner surfaces of the first and second foil sheets for closing the pouch opening and sealing the medical tool or device within the sealed area of the foil pouch. In one embodiment, the supplemental seal extends completely across an upper edge of the foil sheets for sealing the pouch opening and sealing the medical tool or the medical device within a sealed area. The supplemental seal desirably extends across or passes through the roughened surface on at least one of the first and second foil sheets for reducing the amount of force necessary for peeling apart the sheets.

In one embodiment, the pouches may be made from sheets of continuous roll stock. The sheets of continuous roll stock may be feed downstream by a conveyor system to a sealing station at which the sheets are sealed to define a plurality of separate pouches. Each of the pouches may be embossed to provide a textured opening flange on each pouch. The plurality of pouches may then be cut from the roll stock to provide a plurality of separate pouches. After the pouches have been cut into separate pouches, the roughened surfaces at the textured opening flanges physically separate the opposing sheets from one another. The order of steps for sealing, cutting and embossing may be modified as necessary. In one embodiment, the roll stock may be first embossed, then sealed, and then cut into separate pouches. In one embodiment, the pouches are first sealed, then embossed, and then cut into separate pouches. In yet another embodiment, the pouches may be sealed, then cut and then embossed. The latter embodiment may be preferred for non-continuous pouch making operations. The above steps may be performed by a pouch manufacturer to provide a plurality of sealed pouches, with each pouch having a pouch opening adapted to receive a medical device.

After the pouches have been prepared as described above, each of the pouches is ready to receive a medical device such as a flat surgical mesh. In one embodiment, the pouch is finished by inserting the medical device through the pouch opening and into a central sealed area of the pouch. The medical device may be sealed within the pouch by forming a final seal that closes the pouch opening and completely seals the medical device within the pouch. At the same time, the final seal preferably passes through and seals over the textured opening flange. In one embodiment, the final seal may extend along an upper edge of the pouch and pass through the textured flange opening. The pouches are desirable manufactured and sealed in a sterile environment.

In one embodiment, the present invention is directed to packaging for medical devices. It should be clearly understood that, however, that the present invention is not limited thereto and may be embodied in any packaging requirement wherein the features of rapid opening and easy removal of the package contents are desirable.

In one embodiment, the present invention provides an improved pouch design that facilitates the ease of opening the pouch. Conventional packages use weakened seals using patterned coatings (i.e., dot matrix), which weakens the seal (i.e. lowers the force required to separate the two foil layers from each other) and also increases the moisture/oxygen permeation across the seal. The package disclosed herein overcomes these problems in prior art devices.

These and other preferred embodiments of the present invention will be described in more detail below.

BRIEF DESCRIPTION OF THE DRAWING

FIG. 1 shows a pouch for a medical device having a textured opening flange, in accordance with one embodiment of the present invention.

FIGS. 2A-2D show a method of loading a medical device into the pouch of FIG. 1, in accordance with one embodiment of the present invention.

FIGS. 3A-3C show a method of loading a medical device into a pouch having a textured opening flange, in accordance with one embodiment of the present invention.

FIG. 4 shows a pouch having a textured opening flange, in accordance with one embodiment of the present invention.

DETAILED DESCRIPTION

Figure 2C:
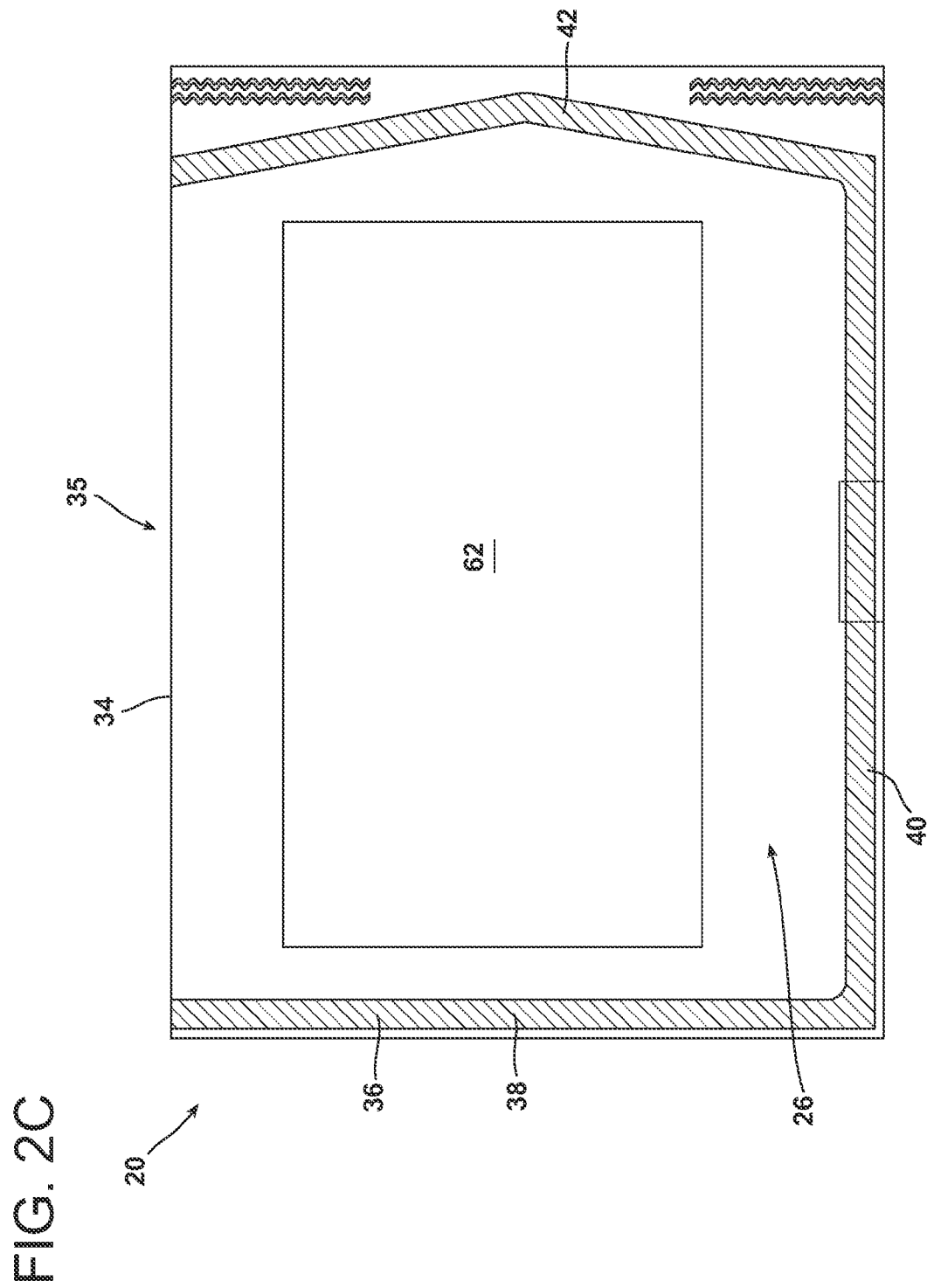

Referring to FIG. 1, in one embodiment, a foil pouch 20 for holding medical tools or medical devices in a sterile environment desirably includes a first foil sheet 22 (FIG. 3A) and a second foil sheet 24 that are joined together to define a sealed area 26 adapted to receive one or more medical tools or medical devices, such as a tissue supporting implant. In one embodiment, the foil pouch preferably includes a leading edge 28, a trailing edge 30, a lower edge 32 that extends between the leading and trailing edges 28, 30, and an upper edge 34 that preferably extends between the leading and trailing edge 28, 30.

In one embodiment, a seal 36 preferably extends adjacent the trailing edge 30, the bottom edge 32 and the leading edge 28 of the pouch. The seal may be formed using adhesive, heat, energy or pressure and combinations thereof. In one embodiment, the seal 36 desirably includes a first leg 38 that extends adjacent the trailing edge 30 and between the upper edge 34 and the lower edge 32, and a second leg 40 that preferably extends adjacent the lower edge 32 and between the trailing edge 30 and the leading edge 28. The seal 36 preferably includes a third leg 42 that desirably extends adjacent the leading edge 28 and between the lower edge 32 and the upper edge 34. In one embodiment, the third leg 24 of the seal 36 preferably includes an apex 44 that divides the third leg 42 into a first section 46 and a second section 48. In one embodiment, the first and second sections 46, 48 of the third leg 42 of the seal are preferably angled relative to one another. In one embodiment, the first section 46 of the third leg 42 defines an angle $A_1$ of about 10-20° and more preferably about 15° with the leading edge 28 of the pouch 20. The second section 48 of the third leg 42 defines an angle of similar scope with the leading edge 28 of the pouch 28.

In one embodiment, the seal 36 has a width $W_1$ of about 5-10 mm and more preferably about 9 mm. In one embodiment, the outer edge 50 of the seal 36 is spaced a distance $D_1$ from the trailing edge 30 and the lower edge 32 of the foil pouch 20. In one embodiment, the distance $D_1$ is about 2-5 mm and more preferably about 3 mm. The apex 44 of the third leg 42 of the seal has an outer edge 52 that defines a distance $D_2$ from the leading edge 28 of the foil pouch 20. In one embodiment, the distance $D_2$ is approximately 5-10 mm and more preferably about 9 mm.

In one embodiment, the pouch 20 preferably includes a textured opening flange 54, which is the area where the foil pouch 20 will be opened. The textured opening flange 54 preferably includes a first textured section 56 that extends adjacent the leading edge 28 of the pouch, from the upper edge 34 toward the lower edge 32. The first textured section 56 is positioned between the second section 48 of the third leg 42 of the seal 36 and the leading edge 28 of the foil pouch 20. As such, the first textured section 56 is located outside the boundary of the seal 36 and does not intersect the seal. In one embodiment, the textured opening flange 54 preferably includes a second textured section 58 that extends adjacent the leading edge 28, from the lower edge 32 toward the upper edge 34 of the foil pouch 20. The second textured section 58 is located between the first section 46 of the third leg 42 of the seal 36 and the leading edge 28 of the foil pouch 20. As such, the second textured section 58 is also located outside the seal 36 and does not intersect with the seal.

In one embodiment, the first and second textured sections 56, 58 are preferably formed by deforming at least one surface of at least one of the foil sheets. The textured sections may also be formed by adhering particles (e.g. sand, gritty elements) to at least one of the first and second sheets. In one embodiment, the first and second textured sections 56, 58 are formed by embossing the foil sheets of the foil pouch 20, such as by using an embossing tool. In addition to providing ease of opening of the pouch at the first and second textured sections, the first and second textured sections 56, 58 also preferably provide a visual marker for indicating the location of the textured opening flange 54 from where the pouch 20 may be opened. Such visual cues are not present in prior art packages having smooth, sealed edges. As will be described in more detail herein, the pouch 20 may be easily opened by peeling the first and second foil sheets away from one another at the textured opening flange 54.

The pouch 20 shown in FIG. 1 may have various shapes and/or dimensions for accommodating medical devices having various sizes, shapes and configurations. In one embodiment, the pouch 20 preferably has a length $L_1$ of approximately 250-400 mm. In one embodiment, the length of the pouch is preferably about 307 mm. The pouch 20 desirably has a height $H_1$ of approximately 100-300 mm. In one embodiment, the height of the pouch is preferably about 227 mm.

In one embodiment, before a medical device is placed in the sealed area 26 of the pouch 20, the upper edge 34 of the pouch 20 remains unsealed for defining a pouch opening 35 that is preferably utilized for placing a medical device inside the pouch. In one embodiment, the length of the pouch opening 35, designated $L_2$, is approximately 150-300 mm. In one embodiment, the pouch opening is preferably about 257 mm. The length $L_2$ of the pouch opening 35 desirably extends between the first leg 38 of the seal 36 and the third leg 46 of the seal 36. In one embodiment, after a medical device is placed inside the pouch through the pouch opening 35, a supplemental seal or fourth leg of the seal may be formed adjacent the upper edges 34 of the sheets to completely seal the sealed area 26 of the pouch. The supplemental seal desirably extends across the entire length $L_1$ of the pouch and between the first leg 38 and the third leg 42 of the seal. The supplemental seal also desirably extends through the first textured opening flange 56.

In one embodiment, a date and time stamp 60 may be placed on the pouch 20 to indicate when the pouch 20 was manufactured. In one embodiment, the date/time indicator 60 is placed adjacent the lower edge 32 of the pouch 20. In one embodiment, the date/time stamp 60 may be used to indicate when the medical device is packaged and sealed in the pouch. The date/time stamp may also provide an expiration date.

In one embodiment, the seal 36 curves between the legs of the seal. In one embodiment, at least one of the curves defines a radius $R_1$ of approximately 5-10 mm and more preferably about 6 mm.

Referring to FIG. 2A, in one embodiment, a pouch 20 having a textured opening flange 54 is prepared to receive a medical device, such as a tissue supporting implant. The seal 36 seals the pouch 20 adjacent the trailing edge 30, the lower edge 32 and the leading edge 28 thereof. The textured opening flange 54 including the first textured section 56 and the second textured section 58 lies outside both the seal 36 and the sealed area 26 of the pouch. The pouch 20 is not sealed adjacent the upper edge 34 of the package so that a pouch opening 35 extends between the first leg 38 of the seal 36 and the third leg 42 of the seal 36.

Referring to FIG. 2B, in one embodiment, a medical device 62 is preferably passed through the pouch opening 35 at the upper edge 34 of the pouch 20. As the medical device 62 passes through the pouch opening 35, the medical device is advanced into the sealed area 26 of the pouch 20.

Referring to FIG. 2C, in one embodiment, the medical device 62 is fully inserted into the sealed area 26 until it is disposed between the first leg 38, the second leg 40 and the third leg 42 of the seal 36. The medical device 62 is preferably positioned so that an upper edge 64 of the medical device 62 lies below the pouch opening 35 at the upper edge 34 of the pouch 20 and completely within the sealed area 26. The medical device may be a tissue supporting implant as disclosed in one or more embodiments of commonly assigned U.S. patent application Ser. No. 12/815,275, filed Jun. 14, 2010, the disclosure of which is hereby incorporated by reference herein. The tissue supporting implant may be placed inside a two component folder before being placed in the pouch. The two component folder is disclosed in one or more embodiments of commonly U.S. patent application Ser. No. 12/820,344, filed Jun. 22, 2010, the disclosure of which is hereby incorporated by reference herein. The pouch may be placed inside a flat outer box as disclosed in commonly assigned U.S. Design patent application Ser. No. 29/364,297, filed Jun. 22, 2010, the disclosure of which is hereby incorporated by reference herein.

Referring to FIG. 2D, in one embodiment, a supplemental seal 66 or fourth leg of the seal 36 is preferably formed to seal the pouch 20 adjacent the upper edge 34 thereof. The supplemental seal 66 desirably extends across the entire length of the upper edge 34 of the pouch 20, crossing the first leg 38 and the third leg 42 of the seal 36 to completely close and seal the sealed area 26 of the pouch. The supplemental seal 66 also desirably includes an extension 68 that crosses the first textured flange opening 56 adjacent the leading edge 28 of the pouch 20. The supplemental seal 66 preferably has a width that substantially matches the width of the first seal 36. In one embodiment, the supplemental seal 66 has an outer edge 70 that is spaced from the upper edge 34 at a distance that is similar to the first seal 36 described above. After the supplemental seal 66 has been formed, the medical device 62 is preferably sealed within the sealed area 26 of the pouch 20. The first seal 36 and the supplemental seal 66 preferably cooperate for maintaining a sterile environment within the sealed area 26.

FIGS. 3A-3C show a method of placing a medical device within the pouch 20, in accordance with one embodiment of the present invention. Referring to FIG. 3A, the pouch 20 is oriented so that the pouch opening 35 at the upper edge 34 is accessible. In one embodiment, the upper edge 34A of the first sheet 22 is spaced from the upper edge 34B of the second sheet 24 to define the pouch opening 35. The seal 36 (FIG. 1) desirably extends adjacent the leading edge 28, the trailing edge 30 and the bottom edge 32 of the pouch for securing the inner surfaces of the first and second sheets 22, 24 together. The textured opening flange 54 including the first textured section 56 and the second textured section 58 lies outside the sealed area, between the third leg 42 (FIG. 1) of the seal and the leading edge 28 of the pouch 20.

Referring to FIG. 3B, in one embodiment, with the first sheet 22 and the second sheet 24 spaced from one another along the upper edge 34 of the foil pouch 20 for providing the pouch opening 35, the medical device 62 is inserted into the pouch opening 35. Referring to FIG. 3C, after the medical device 62 is fully inserted into the sealed area 26 of the pouch 20, the supplemental seal 66 (FIG. 2D) may be formed across the upper edges of the first and second sheets 22, 24 for closing the pouch opening 35 and completely sealing the medical device 62 within the pouch 20.

Referring to FIG. 4, in one embodiment, a pouch 20 for a medical device preferably includes a leading edge 28, a trailing edge 30, a lower edge 32 and an upper edge 34. The pouch 20 desirably includes a closed seal for sealing a medical device inside the pouch 20. The seal preferably includes a chevron-shaped leg 42 that extends near the leading edge 28 of the pouch. The chevron-shaped leg 42 preferably includes an apex 44 that is located between a first textured section 56 and a second textured section 58 of a textured opening flange 54. The first and second textured sections 56, 58 are desirably located outside the sealed area 26 (FIG. 1) of the pouch 20 and specifically outside the chevron-shaped leg 42 of the seal.

Although the present invention is not limited by any particular theory of operation, it is believed that providing a textured opening flange 54 including first and second textured sections 56, 58 outside the seal will prevent the integrity of the seal from being minimized or violated. In addition, the textured opening flange including the first and second textured sections 56, 58 makes it easier to open the pouch 20, particularly when the supplemental seal for closing the pouch opening passes through one of the textured sections of the textured opening flange 54. The textured opening flange 54 also desirably provides an indication of which end of the foil pouch is to be opened.

Figure 5:
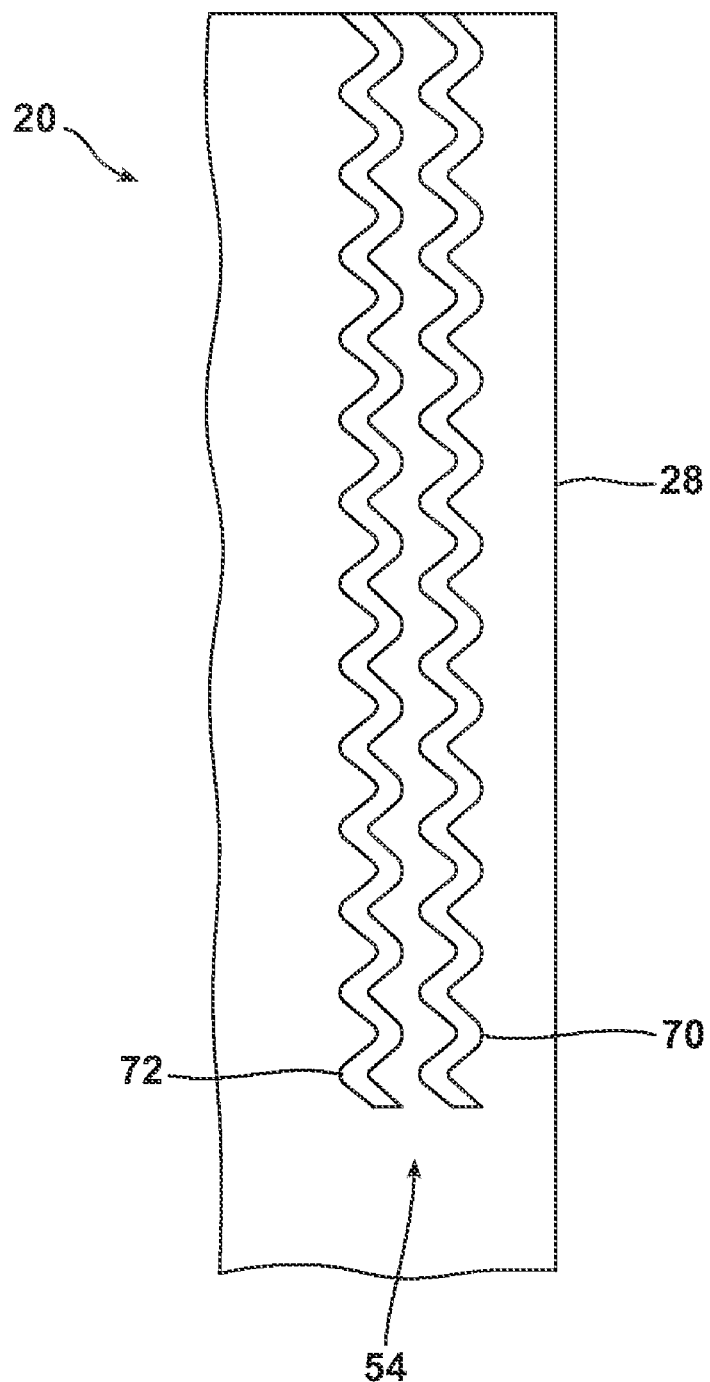
FIG. 5 shows a magnified view of a first section of the textured opening flange of FIG. 4.

FIG. 5 shows a magnified view of the first textured section 56 of the textured opening flange 54. In one embodiment, the first textured section 56 is formed by deforming the surfaces of the first and second sheets of the pouch using a tool, such as embossing tools. In one embodiment, the tool desirably mechanically alters the texture of the first and second sheets. In one embodiment, the texturing or roughened surface is formed on only one of the sheets. In another embodiment, however, the texturing or roughening is preferably formed on both of the first and second sheets. In the particular embodiment shown in FIG. 5, the first textured section 56 includes a first textured row 70 and a second textured row 72 that extends adjacent the first textured row 70. The first and second textured rows 70, 72 preferably extend parallel to the leading edge 28 of the pouch 20. In one embodiment, the textured rows 70, 72 have a width of approximately 0.05-0.10 inches and more preferably about 0.06 inches. In one embodiment, the mechanical deformations formed in the first and second sheets have a depth of about 0.025-0.075 inches and more preferably about 0.04 inches.

Figure 6:
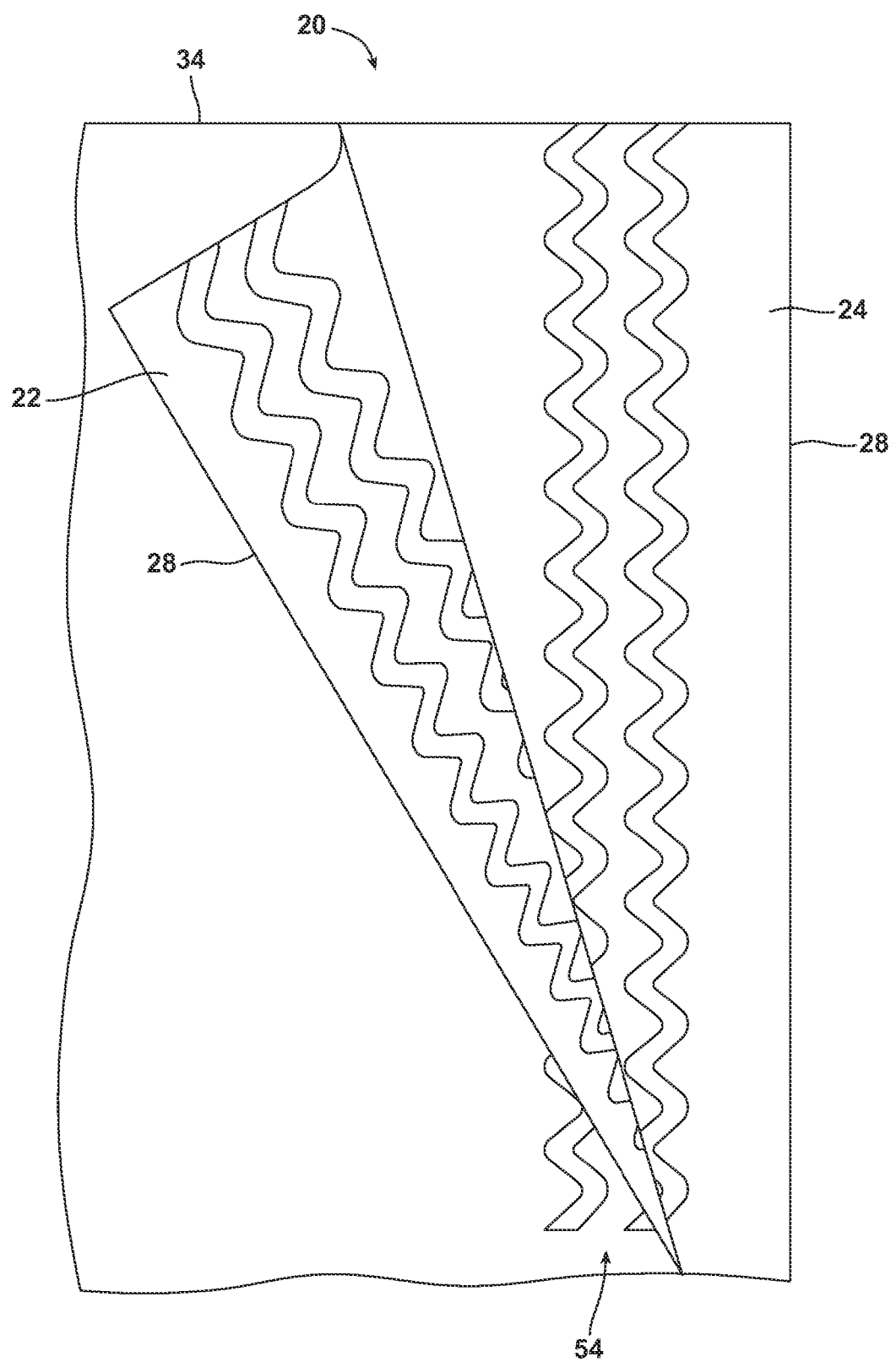
FIG. 6 shows a textured opening flange for a pouch with two sheets being pulled away from one another for opening the pouch, in accordance with one embodiment of the present invention.

Referring to FIG. 6, in one embodiment, the first textured section 56 includes mechanical deformations formed in both the first sheet 22 and the second sheet 24. The mechanical deformations preferably extend adjacent the leading edges 28 of the respective first and second sheets 22, 24 and from the upper edge 34 of the pouch toward the lower edge thereof. In FIG. 6, the first textured section 56 preferably provides a textured opening flange 54 that enables the pouch to be easily opened. More specifically, the textured opening flange 54 including the first textured section 56 enables the first sheet 22 and the second sheet 24 to be more easily peeled away from one another, even when a seal extends through the first textured section. Thus, the textured opening flange enables surgical personnel to begin to open the sealed pouch. Once sufficient areas of the first and second sheets 22, 24 have been peeled away from one another, an operator may more easily pull the remainder of the first and second sheets away from one another so as to break open the seal protecting the sealed area of the pouch.

Figure 7:
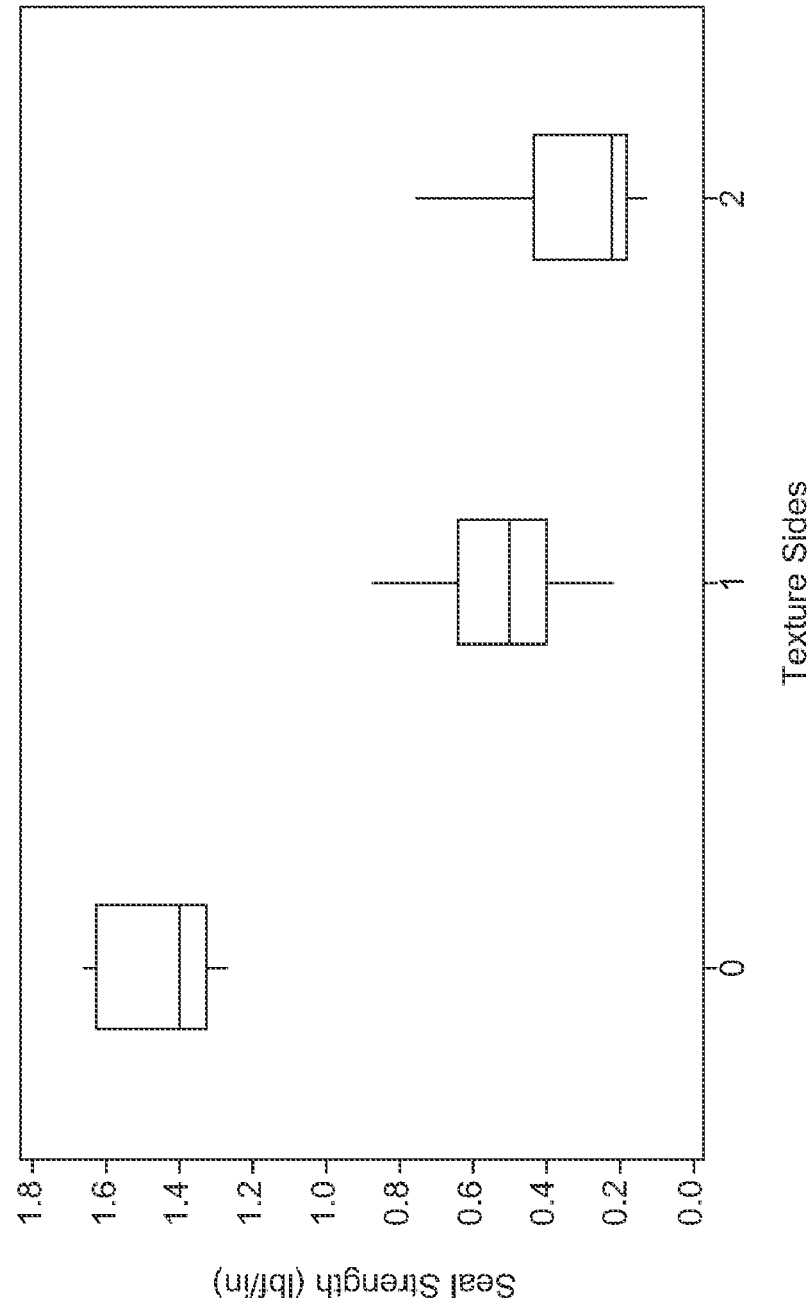
FIG. 7 shows a graph plotting the respective seal strengths of a flat seal, a one-side texture seal, and a two-side textured seal, in accordance with one embodiment of the present invention.

FIG. 7 is a graph plotting the seal strength of a textured seal versus a flat seal with no texturing or roughened surface. As shown in the graph of FIG. 7, when two sheets are sealed together as a flat seal with no texturing or roughened surface, the flat seal strength is about 1.4 lbf/in. When one of the sheets is textured or has a roughened surface, the textured seal strength is reduced to about 0.5 lbf/in. When both of the first and second sheets are textured or have roughened surfaces, the textured seal strength is further reduced to less than 0.5 lbf/in.

Using a textured opening flange provides a number of benefits over prior art devices. As shown in FIG. 7, with the supplemental seal extending through the textured opening flange, the roughened surfaces of the textured opening flange reduce the amount of force required to peel open a package such as a foil pouch, thereby enabling medical personnel to more easily open the package. The textured opening flange also desirably provides a visual marker that may be used for indicating which side of the package is to be opened. Moreover, in one embodiment, the first and second textured sections 56, 58 may have a proprietary design or pattern embossed therein to differentiate an original product from a counterfeit product, thereby making counterfeiting more difficult. In addition, by locating the textured opening flange outside the central sealed area containing the medical tool or device, the integrity of the sealed area is not compromised.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A pouch having a textured opening flange comprising:
first and second sheets having opposing inner surfaces joined together by a seal for defining a sealed area of said pouch located inside said seal and an unsealed area of said pouch located outside said seal;
said textured opening flange located adjacent an edge of said pouch for peeling said first and second sheets away from one another for breaking said seal and opening said sealed pouch, said textured opening flange being located within said unsealed area of said pouch and including at least one roughened surface formed on at least one of said first and second sheets, wherein a leg of said seal extends into said unsealed area of said pouch and passes through said textured opening flange.

2. The pouch as claimed in claim 1, wherein said pouch comprises a foil pouch and said first and second sheets comprise foil sheets.

3. The pouch as claimed in claim 1, wherein said pouch includes a leading edge, a trailing edge, a lower edge and an upper edge, and wherein said textured opening flange is located adjacent said leading edge of said pouch.

4. The pouch as claimed in claim 3, wherein said textured opening flange is located between said sealed area and said leading edge of said pouch.

5. The pouch as claimed in claim 1, wherein said at least one roughened surface is adjacent said leading edge of said pouch.

6. The pouch as claimed in claim 5, wherein said at least one roughened surface extends parallel with said leading edge of said pouch.

7. The pouch as claimed in claim 6, wherein said at least one roughened surface includes a first roughened section extending from said upper edge of said pouch and a second roughened section extending from said lower edge of said pouch.

8. The pouch as claimed in claim 4, wherein said seal includes a first leg extending adjacent said trailing edge of said pouch, a second leg extending adjacent said lower edge of said pouch, a third leg extending adjacent said leading edge of said pouch and said leg extending adjacent said upper edge of said pouch.

9. The pouch as claimed in claim 8, wherein said leg of said seal extends completely across said upper edge of said pouch and through said textured opening flange.

10. The pouch as claimed in claim 8, wherein said first, second and third legs of said seal have outer perimeters that are spaced from said respective trailing, lower and upper edges of said pouch.

11. The pouch as claimed in claim 10, wherein said outer perimeter of said first leg of said seal is spaced about 2-5 mm from said trailing edge of said pouch, said outer perimeter of said second leg of said seal is spaced about 2-5 mm from said lower edge of said pouch, and said outer perimeter of said leg of said seal is spaced about 2-5 mm from said upper edge of said pouch.

12. The pouch as claimed in claim 11, wherein said leading edge of said pouch includes a first end located adjacent said upper edge of said pouch, a second end located adjacent said lower edge of said pouch and a center located between said first and second ends of said leading edge, and wherein said third leg of said seal is non-linear and includes an apex aligned with said center of said leading edge, a first section extending between said apex of said third leg and said upper edge of said pouch and a second section extending between said apex of said third leg and said lower edge of said pouch.

13. The pouch as claimed in claim 12, wherein said first section of said third leg extends along an axis that defines a first angle with said leading edge of said pouch and said second section of said third leg extends along a second axis that defines a second angle with said leading edge of said pouch.

14. The pouch as claimed in claim 1, wherein said at least one roughened surface comprises a first roughened surface formed in said first sheet and a second roughened surface formed in said second sheet that is aligned with said first roughened surface.

15. The pouch as claimed in claim 1, wherein said at least one roughened surface comprises deformations formed in at least one surface of at least one of said first and second sheets.

16. The pouch as claimed in claim 1, wherein said at least one roughened surface comprises an embossed surface.

17. A sealed foil pouch having a textured opening flange comprising:
first and second foil sheets having opposing inner surfaces joined together by a seal for defining a sealed area of said foil pouch located inside said seal and an unsealed area of said foil pouch located outside said seal;
said textured opening flange located adjacent an edge of said foil pouch for peeling said first and second foil sheets away from one another for breaking said seal and opening said sealed foil pouch, said textured opening flange being located within said unsealed area of said foil pouch and including at least one roughened surface formed on at least one of said first and second foil sheets, wherein a leg of said seal passes through said textured opening flange.

18. The sealed foil pouch as claimed in claim 17, further comprising a medical device disposed within said sealed area of said foil pouch, wherein said medical device is removable from said foil pouch by peeling said first and second foil sheets away from one another for breaking said seal and opening said pouch.

19. The sealed foil pouch as claimed in claim 17, wherein said textured opening flange comprises a first pull tab located on said first foil sheet and a second pull tab located on said second foil sheet, wherein said first and second pull tabs are peelable away from one another for facilitating grasping of said first and second foil sheets.

20. The sealed foil pouch as claimed in claim 17, wherein said seal includes a first leg extending adjacent said trailing edge of said foil pouch, a second leg extending adjacent said lower edge of said foil pouch, a third leg extending adjacent said leading edge of said foil pouch and said leg extending adjacent said upper edge of said foil pouch, wherein said first, second and third legs of said seal have outer perimeters that are spaced from said respective trailing, lower and upper edges of said foil pouch, and wherein said leading edge of said foil pouch includes a first end located adjacent said upper edge of said foil pouch, a second end located adjacent said lower edge of said foil pouch and a center located between said first and second ends of said leading edge, and wherein said third leg of said seal is non-linear and includes an apex aligned with said center of said leading edge, a first section extending between said apex of said third leg and said upper edge of said foil pouch and a second section extending between said apex of said third leg and said lower edge of said foil pouch, said first section of said third leg extending along an axis that defines a first angle with said leading edge of said foil pouch and said second section of said third leg extends along a second axis that defines a second angle with said leading edge of said foil pouch.

* * * * *